(12) United States Patent
Brower

(10) Patent No.: US 11,639,862 B1
(45) Date of Patent: May 2, 2023

(54) APPARATUS, SYSTEM AND METHOD ENABLING MULTIPLEXED ARRANGEMENT OF OPTICAL FIBER FOR SENSING OF OPERATING CONDITIONS WITHIN A STRUCTURAL MEMBER

(71) Applicant: David V Brower, Houston, TX (US)

(72) Inventor: David V Brower, Houston, TX (US)

(73) Assignee: Astro Technology Group, LLC, Houston, TX (US)

( * ) Notice: Subject to any disclaimer, the term of this patent is extended or adjusted under 35 U.S.C. 154(b) by 0 days.

(21) Appl. No.: 15/334,673

(22) Filed: Oct. 26, 2016

Related U.S. Application Data

(63) Continuation-in-part of application No. 13/852,896, filed on Mar. 28, 2013, now abandoned, which is a continuation of application No. 12/882,993, filed on Sep. 15, 2010, now abandoned.

(60) Provisional application No. 61/242,746, filed on Sep. 15, 2009.

(51) Int. Cl.
| | |
|---|---|
| *G02B 6/50* | (2006.01) |
| *G01D 5/26* | (2006.01) |
| *G01J 1/44* | (2006.01) |
| *G01J 1/02* | (2006.01) |

(52) U.S. Cl.
CPC ............ *G01D 5/268* (2013.01); *G01J 1/0228* (2013.01); *G01J 1/44* (2013.01); *G02B 6/506* (2013.01)

(58) Field of Classification Search
CPC ................................. G02B 6/506; G01D 5/268
See application file for complete search history.

(56) References Cited

U.S. PATENT DOCUMENTS

| | | | | |
|---|---|---|---|---|
| 4,477,725 A | * | 10/1984 | Asawa | G01L 1/245 250/231.19 |
| 6,489,606 B1 | * | 12/2002 | Kersey | G01L 1/246 385/13 |
| 6,588,266 B2 | * | 7/2003 | Tubel | E21B 47/00 73/152.43 |
| 6,876,786 B2 | * | 4/2005 | Chliaguine | G01D 5/35303 356/73.1 |
| 9,915,579 B1 | * | 3/2018 | Brower | G01L 11/025 |
| 2003/0072514 A1 | * | 4/2003 | Ames | G01D 5/35383 385/12 |

* cited by examiner

*Primary Examiner* — Daniel Petkovsek
(74) *Attorney, Agent, or Firm* — IVC Patent Agency; David O. Simmons

(57) ABSTRACT

Embodiments of the present invention provide a unique new approach to generating operating condition information used for assessing flow assurance and structural integrity. More specifically, apparatuses, systems and methods configured in accordance with embodiments of the present invention enable multiplexed arrangement of optical fiber for sensing of operating conditions within a structural member and utilize fiber optic sensors for enabling monitoring of operating condition information within one or more elongated tubular members. To this end, fiber optic sensors are strategically placed at a plurality of locations along a length of each elongated tubular member thereby allowing critical operating conditions such as strain, temperature and pressure of the elongated tubular member and/or a fluid therein to be monitored. A multiplexing unit is used for allowing selective configuration of individual lengths of optical fiber for creating one or more contiguous optical fiber structures.

13 Claims, 17 Drawing Sheets

APPARATUS, SYSTEM AND METHOD ENABLING MULTIPLEXED ARRANGEMENT OF OPTICAL FIBER FOR SENSING OF OPERATING CONDITIONS WITHIN A STRUCTURAL MEMBER

CROSS-REFERENCE TO RELATED APPLICATIONS

This continuation-in-part patent application claims priority from co-pending United States non-provisional patent application having Ser. No. 13/852,896, filed 23 Mar. 2013, entitled "AN APPARATUS TO MONITOR FLOW ASSURANCE PROPERTIES IN CONDUITS", having a common applicant herewith and being incorporated herein in its entirety by reference.

United States non-provisional patent application having Ser. No. 13/852,896 is a continuation of and claims priority from co-pending United States non-provisional patent application having Ser. No. 12/882,993 filed 15 Sep. 2010, entitled "APPARATUS TO MONITOR FLOW ASSURANCE PROPERTIES IN CONDUITS", having a common applicant therewith and being incorporated herein in its entirety by reference.

United States non-provisional patent application having Ser. No. 12/882,993, claims priority from co-pending United States provisional patent application having Ser. No. 61/242,746, filed 15 Sep. 2009, entitled "APPARATUS TO MONITOR FLOW ASSURANCE PROPERTIES IN CONDUITS", having a common applicant therewith and being incorporated herein in its entirety by reference.

FIELD OF THE DISCLOSURE

The disclosures made herein relate generally to monitoring of operating conditions within structural members and, more particularly, to apparatuses, systems and methods enabling multiplexed arrangement of optical fiber for sensing of operating conditions within a structural member.

BACKGROUND

Structural members for which it is necessary to monitor operating condition information thereof are well-known and are used in many industries and applications. Such structural members can have a solid cross sectional construction or have an interior space. An elongated tubular member (e.g., a pipe) is an example of such a structural member with an interior space. Elongated tubular members used in offshore drilling and production systems in the oil and gas industry are a prime example of structural members for which it is necessary to monitor operating condition information thereof.

Offshore drilling and production systems include a work platform at a sea surface (i.e., a surface work platform) that is in communication with a production field beneath the seafloor. A first type of conduit, which is generally referred to a riser, is required to support equipment and materials being delivered from the surface work platform to the subsea field, and/or a conduit for lifting oil and gas being produced from the subsea field to the surface work platform. A second type of conduit, which his generally referred to as a pipeline, links wellheads to a processing site. These conduits are examples of elongated tubular members.

Many pipelines are deployed in subsea environments where water temperatures can cool the all or a portion of the pipeline that carries the hydrocarbon from the wellhead to the processing site. As hot gases that flow from the wellhead (i.e., particularly subsea wellheads) are subjected to cooling, hydrates can precipitate from the product and results in flow restrictions and in extreme cases can completely block the pipeline. In other instances, slow buildup of paraffin wax on the interior of the pipeline can cause flow restrictions. These blockages and flow restrictions pose significant risk to safe and efficient operation of such pipelines.

Tension leg platforms, floating rigs, jack-up rigs and other known offshore drilling and production systems are examples of surface work platforms. In many of these systems, in addition to the aforementioned types of conduits, some sort of legs or equivalent platform support structures extends from the sea floor to the surface work platform. These platform support structures generally have a tubular construction and are, thus, another example of a tubular structural member.

A tension leg platform (TLP) is a specific example of a surface work platform having conduits and platform support structures (i.e., tubular structural members) for which operating conditions need to be monitored. A TLP, which is a permanently positioned structure used for the production of oil and gas in offshore environments, uses platform support structures in the form of tension legs (i.e., also referred to as tendons) to support the platform above the sea surface. TLPs, which are typically used in water depths ranging from 1000 to 5000 feet, are secured in place using tension legs that each have a first end attached to a respective portion (e.g., corner) of a platform portion of the TLP and that have a second end that is attached to a respective piling that has been driven into the sea floor. Tension legs of a TLP are typically made of tubular steel. In order for the TLP to work properly, the tension legs are kept under a relatively high level of tension. Such implementation of the tension legs restricts vertical motion of the platform that would otherwise occur due to tides and wave action. A major advantage of TLPs is that the wellhead can be placed on the surface rather than on the sea floor, thereby giving better access and simpler production control.

In a typical TLP installation, three load sensors are installed into the tendon top connector assembly, which is on a sub-platform or bridge for each tendon, below the primary work platform. The data from these load sensors is then used to calculate the maximum, minimum and mean tensions and standard deviation in the tendon, together with the bending movement angle. Historically, the load cells are unreliable and often fail early in their service life such as due to their exposure to seawater and other harsh environmental conditions.

Elongated tubular members such as tension legs, risers and pipelines are subject to environmental conditions such as the flow, wave action and temperature of the surrounding seawater. These environmental conditions effect operating conditions such as, for example, tension, bending, compressive forces, expansion and contraction due to changes in water temperature, internal pressure of fluids within the risers, and other operating conditions strains and stresses to which the elongated tubular members are subjected. To ensure safe and reliable operation of such elongated tubular members, an operating condition monitoring system is required to provide reliable measurement of operating condition information in each of the elongated tubular members and output such operating condition information, preferably in real-time. When the monitoring system fails, it is often necessary to shut down the drilling or production system at significant expense such has due to lost revenue and loss of drilling or production time As is well-known, it is desirable to operate drilling and production systems in a safe, reliable, predictable and efficient manner. To this end, it is beneficial to monitor operating condition information of elongated tubular members of such drilling and production systems, whether offshore-based or land-based. Examples of operating condition include, but are not limited to, strain within a wall of an elongated tubular members, pressure within an interior space of the elongated tubular members, torsion applied to the elongated tubular members, temperature of the wall or surface of the elongated tubular members, temperature of a fluid within the interior space of the elongated tubular members, and flow confirmation of a fluid within the interior space of the elongated tubular members.

Various devices and systems have been deployed to generate and monitor operating condition information. Examples of these devices and systems include, but are not limited to, load cells on TLP tension legs, mechanical strain gauges on risers and pipelines, invasive sensors on risers and pipelines (e.g., which penetrate the conduit), and other types of devices and systems. These types of prior art devices and systems are of limited functional value in that they provide less than optimal operating condition information, are subject to early fatigue caused by the rigorous environmental conditions in which they are employed, and often undesirably require invasive installation techniques.

Therefore, apparatuses, systems and sensor housing assemblies that utilize fiber optic sensors for enabling monitoring of operating condition information within one or more elongated tubular members to overcome drawbacks associated with conventional approaches for generating and monitoring operating condition information would be advantageous, desirable and useful.

SUMMARY OF THE DISCLOSURE

Embodiments of the present invention provide a unique approach to generating operating condition information used for assessing flow assurance and structural integrity. More specifically, apparatuses, systems and sensor housing assemblies configured in accordance with embodiments of the present invention utilize fiber optic sensors for enabling monitoring of operating condition information within one or more elongated tubular members. To this end, such fiber optic sensors can be strategically placed at a plurality of locations along a length of each elongated tubular member thereby allowing critical operating conditions such as strain, temperature and pressure of the elongated tubular member and/or a fluid therein to be monitored.

Advantageously, embodiments of the present invention provide a simple yet effective and reliable approach of monitoring operating conditions along elongated tubular members that can be on the order of 70 miles or more. Furthermore, embodiments of the present invention advantageously allow for such fiber optic sensors to be installed before or after deployment of the elongated tubular members. In preferred embodiments, the fiber optic sensors are integrated into respective sensor housing, which allow a plurality of fiber optic sensors to the mounted on an elongated tubular member through mounting of the sensor housing thereon. Operating condition information from the fiber optic sensors of a plurality of sensor housings is communicated to a data acquisition system through one or more optical fibers.

In one embodiment of the present invention, an apparatus for sensing operating condition information from an elongated tubular member comprises a plurality of tubular member interface bodies, a plurality of optical fibers, an optical sensing module, and a multiplexing unit. Each one of the tubular member interface bodies includes a tubular member engagement portion and an optical fiber engagement portion. Each one of the optical fibers has a first end and a second end. Two or more of the optical fibers have at least one operating condition signal generating portion between the first and second ends thereof. The at least one operating condition signal generating portion of the two or more of the optical fibers is attached along a length of the optical fiber engagement portion of a respective one of the tubular member interface bodies to thereby form a plurality of operating condition sensors connected to the elongated tubular member. The optical sensing module has at least one signaling port. The multiplexing unit includes a plurality of optical fiber interfaces each having a downstream facing port and an upstream facing port. The upstream facing port of each one of the optical fiber interfaces is connectable to each other one of the upstream facing ports. Each end of each one of the optical fibers is operably connected to the downstream facing port of a respective one of the optical fiber interfaces. The upstream facing ports are connected to each other such that at least two of the optical fibers are connected to each in a series fashion to form a contiguous optical fiber structure having opposing ends. The upstream facing port connected to an end of the contiguous optical fiber structure is connected to the at least one signaling port of the optical sensing module for enabling sensor data generated within the contiguous optical fiber structure to be provided from the multiplexing unit to the optical sensing module.

In another embodiment of the present invention, a method of collecting operating condition information from an elongated tubular member comprises a plurality of operations. An operation is performed for monitoring an operating condition signal provided at one of opposing ends of a contiguous optical fiber structure to determine operating condition information generated by a plurality of operating condition sensors connected to the elongated tubular member. The contiguous optical fiber structure comprises a plurality of individual lengths of optical fiber connected in an end-to-end fashion to form a single length of optical fiber having the opposing ends. At least two of the individual lengths of optical fiber includes at least one of the operating condition sensors integral therewith between opposing ends thereof. An operation is performed for detecting, via the operating condition signal, loss of operating condition information corresponding to at least one of the individual lengths of optical fiber. In response to detecting the loss of operating condition information, an operation is performed for reconfiguring monitoring of the operating condition signal. Reconfiguring such monitoring includes one of causing an operating condition signal to be provided at both of the opposing ends of the contiguous optical fiber structure and monitoring a respective operating condition signal at both of the ends of the contiguous optical fiber structure and excluding the at least one of the individual lengths of optical fiber from within the contiguous optical fiber structure to create a reconfigured version of the contiguous optical fiber structure and continuing to monitor the operating condition signal provided at the one of the opposing ends of the contiguous optical fiber structure.

In another embodiment of the present invention, a system comprises a plurality of operating condition sensors, an optical sensing module, and a multiplexing unit. The operating condition sensors are connected to an elongated tubular member. Each one of the operating condition sensors includes a plurality of an operating condition signal generating portion of a respective one of a plurality of optical fibers each having a first end and a second end. The optical sensing module has at least one signaling port. The multiplexing unit includes a plurality of optical fiber interfaces each having a downstream facing port and an upstream facing port. The upstream facing port of each one of the optical fiber interfaces is connectable to each other one of the upstream facing ports. Each end of each one of the optical fibers is operably connected to the downstream facing port of a respective one of the optical fiber interfaces. The upstream facing ports are connected to each other such that at least two of the optical fibers are connected to each in a series fashion to form a contiguous optical fiber structure having opposing ends. The upstream facing port connected to an end of the contiguous optical fiber structure is connected to the at least one signaling port of the optical sensing module for enabling sensor data generated within the contiguous optical fiber structure to be provided from the multiplexing unit to the optical sensing module.

These and other objects, embodiments, advantages and/or distinctions of the present invention will become readily apparent upon further review of the following specification, associated drawings and appended claims.

DETAILED DESCRIPTION

Figure 1:
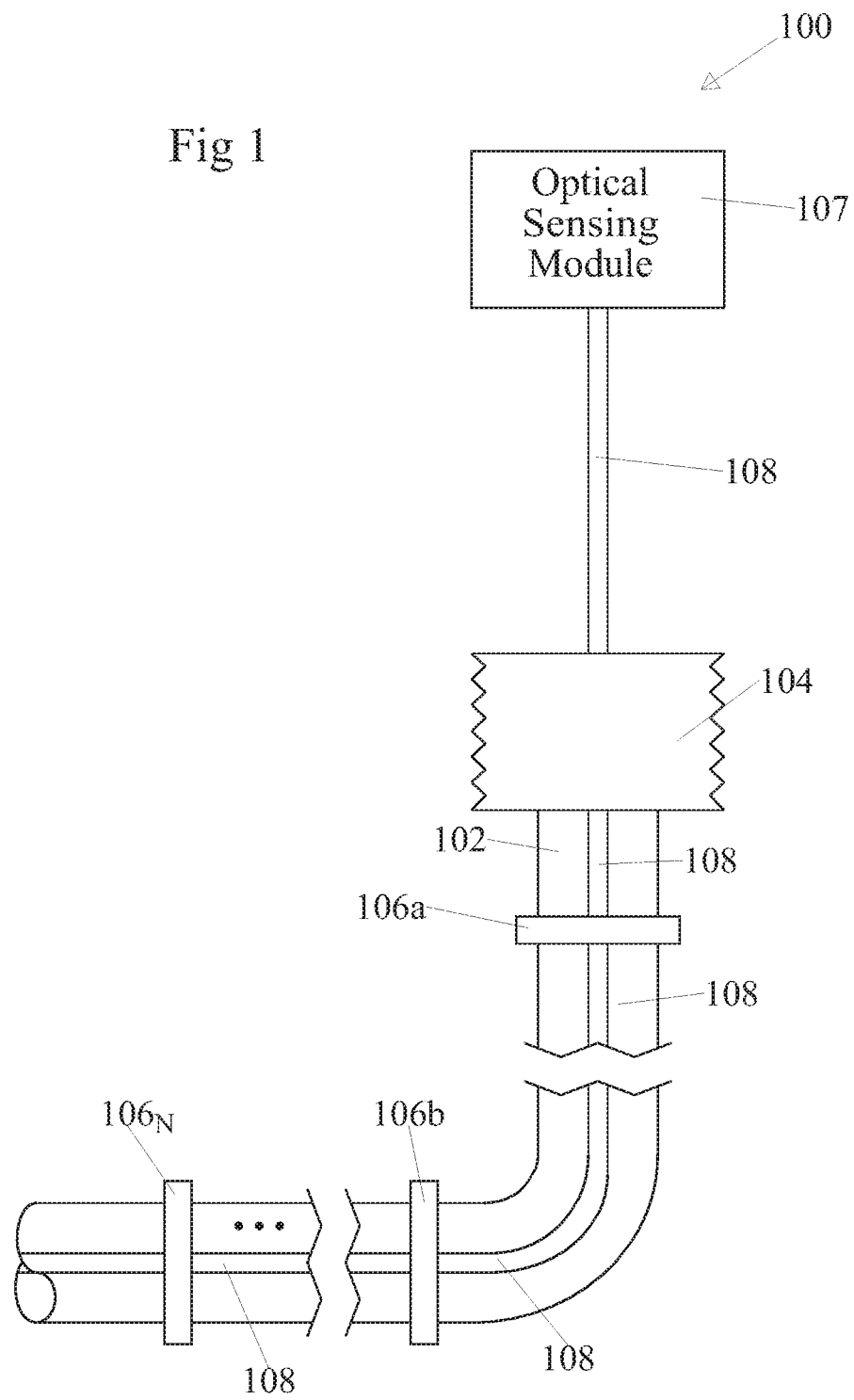
FIG. 1 is a diagrammatic view showing an operating condition monitoring apparatus configured in accordance with an embodiment of the present invention.

FIG. 1 shows an apparatus 100 configured in accordance with an embodiment of the present invention. The apparatus 100 includes an elongated tubular member 102 that is connected to a support structure 104. A plurality of sensor housing assemblies 106a-106n are mounted in a spaced-apart arrangement along a length of the elongated tubular member 102. The sensor housing assemblies 106a-106n are connected to each other and to an optical sensing module 107, such as at a signaling port thereof, by a fiberoptic cable 108.

The sensor housing assemblies 106a-106n, the optical sensing module 107 and the fiberoptic cable 108 jointly provide for operating condition information for the elongated tubular member 102, a fluid within the elongated tubular member 102, or both to be generated, communicated and monitored. As discussed below in greater detail, each one of the sensor housing assemblies 106a-106n includes one or more fiber optic sensors (not specifically shown in FIG. 1) that are configured for generating specific respective operating condition information. Examples of such operating condition information includes, but is not limited to, strain within a wall of the elongated tubular member 102, pressure within an interior space of the elongated tubular member 102, torsion applied to the elongated tubular member 102, temperature of the wall or surface of the elongated tubular member 102, temperature of a fluid within the interior space of the elongated tubular member 102, and flow confirmation of a fluid within the interior space of the elongated tubular member 102.

Embodiments of the present invention are not limited to any particular elongated tubular member 102 or support structure 104. However, in many applications, a given elongated tubular member will typically be used in association with a corresponding support structure. For example, where the support structure is a tension leg platform (TLP), an elongated tubular member thereof may be a tension leg or a riser. In another example, where the support structure is a wellhead, an elongated tubular member thereof may be a pipeline or the like.

Figure 2:
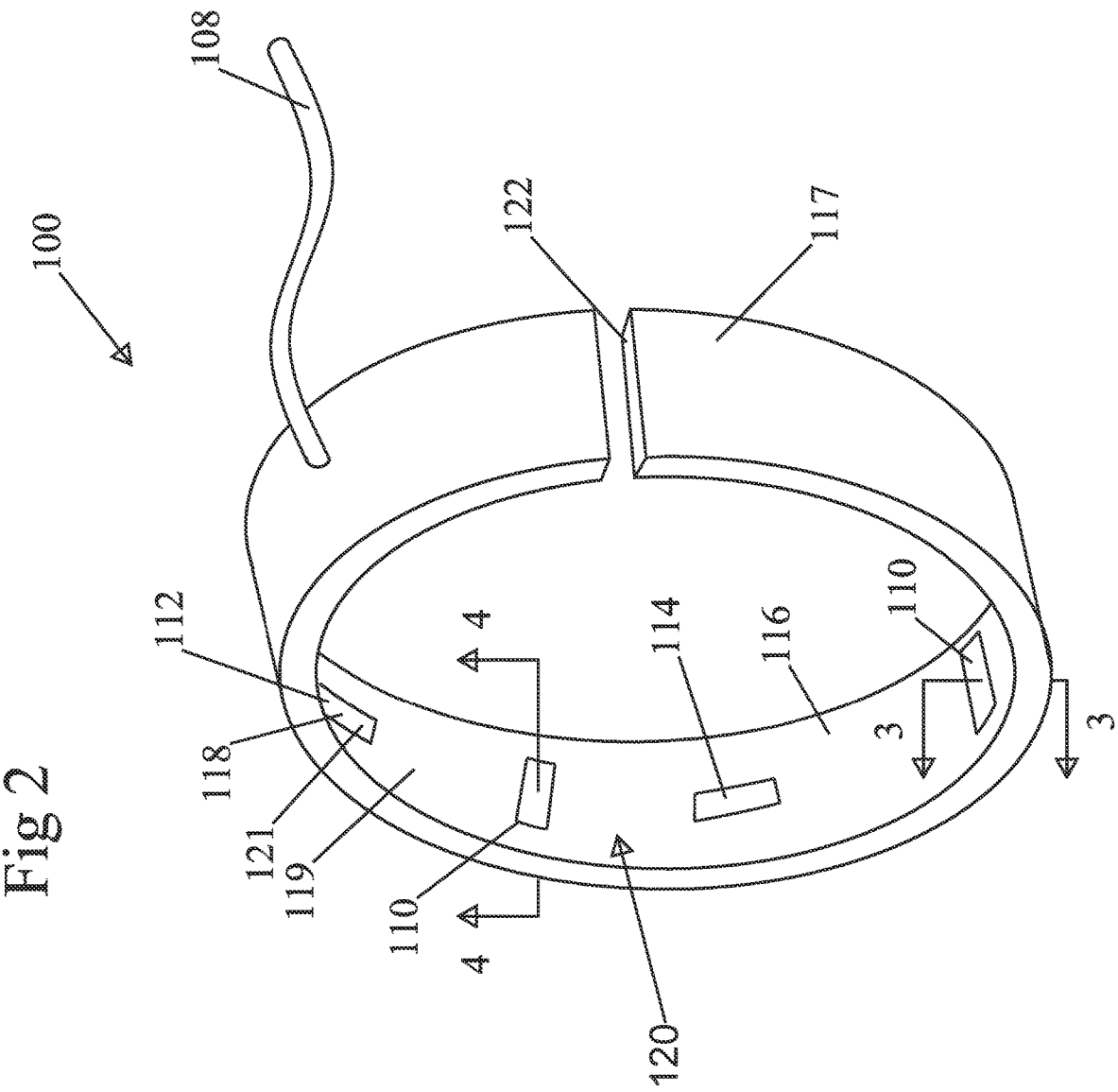
FIG. 2 is a perspective view of a sensor housing assembly configured in accordance with an embodiment of the present invention.
Figure 3:
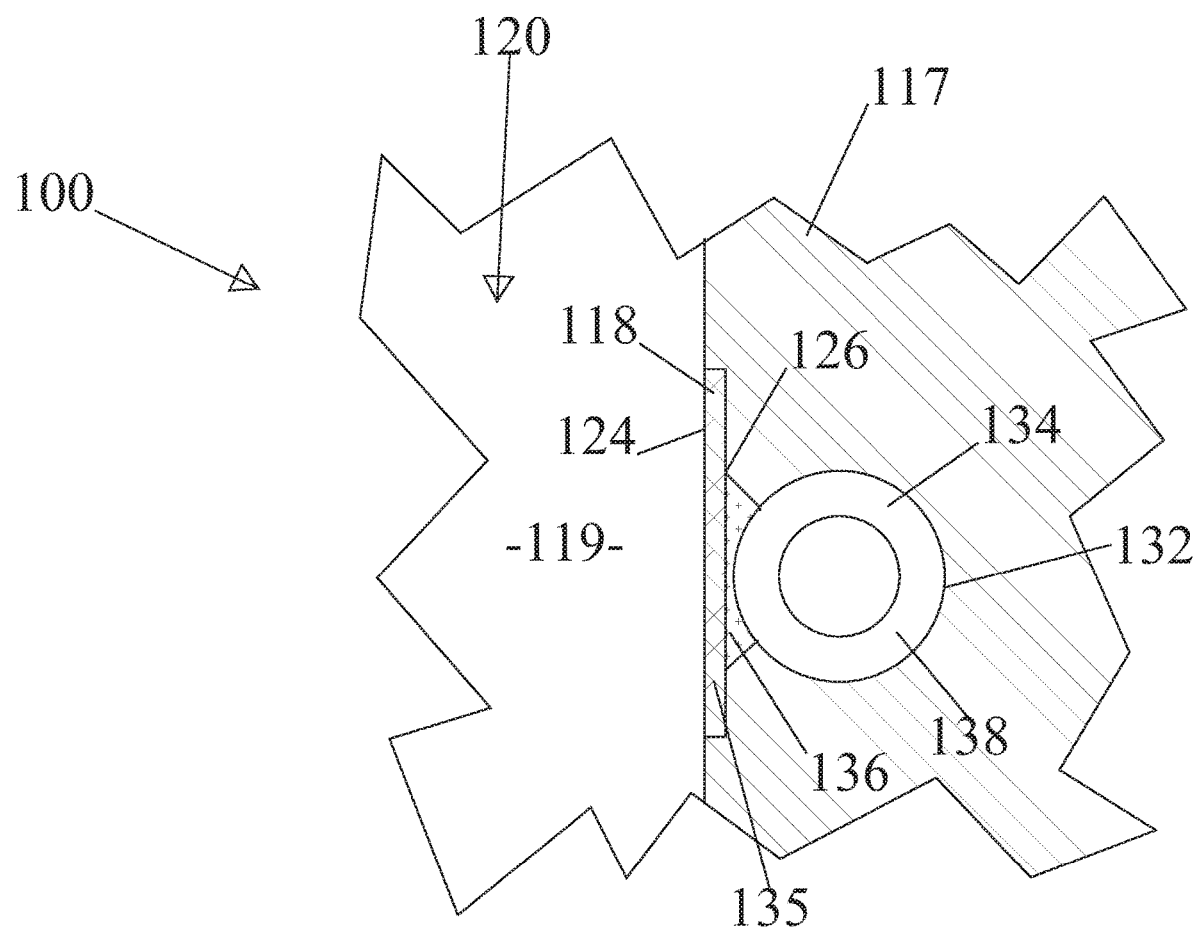
FIG. 3 is a fragmentary cross-sectional view taken along the line 3-3 in FIG. 2.
Figure 4:
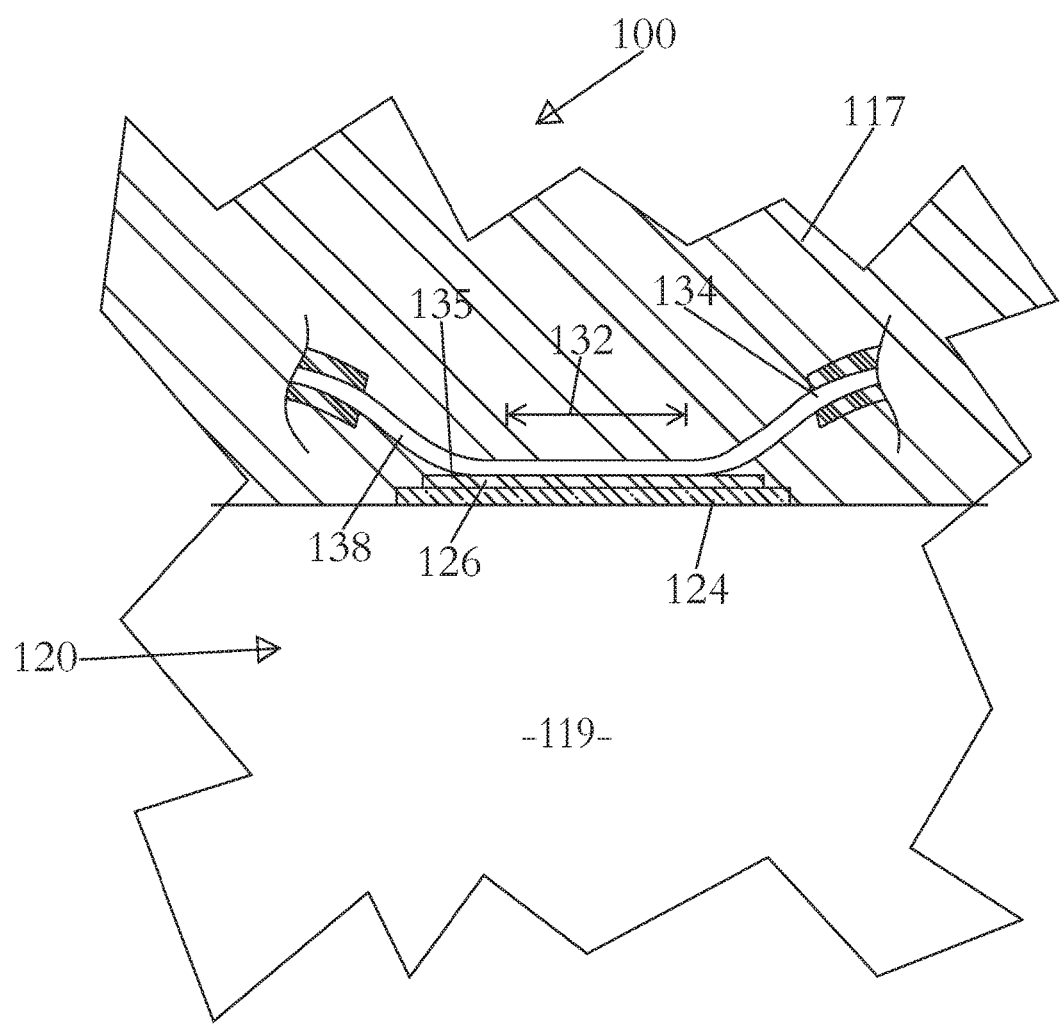
FIG. 4 is a fragmentary cross-sectional view taken along the line 4-4 in FIG. 2.
Figure 5:
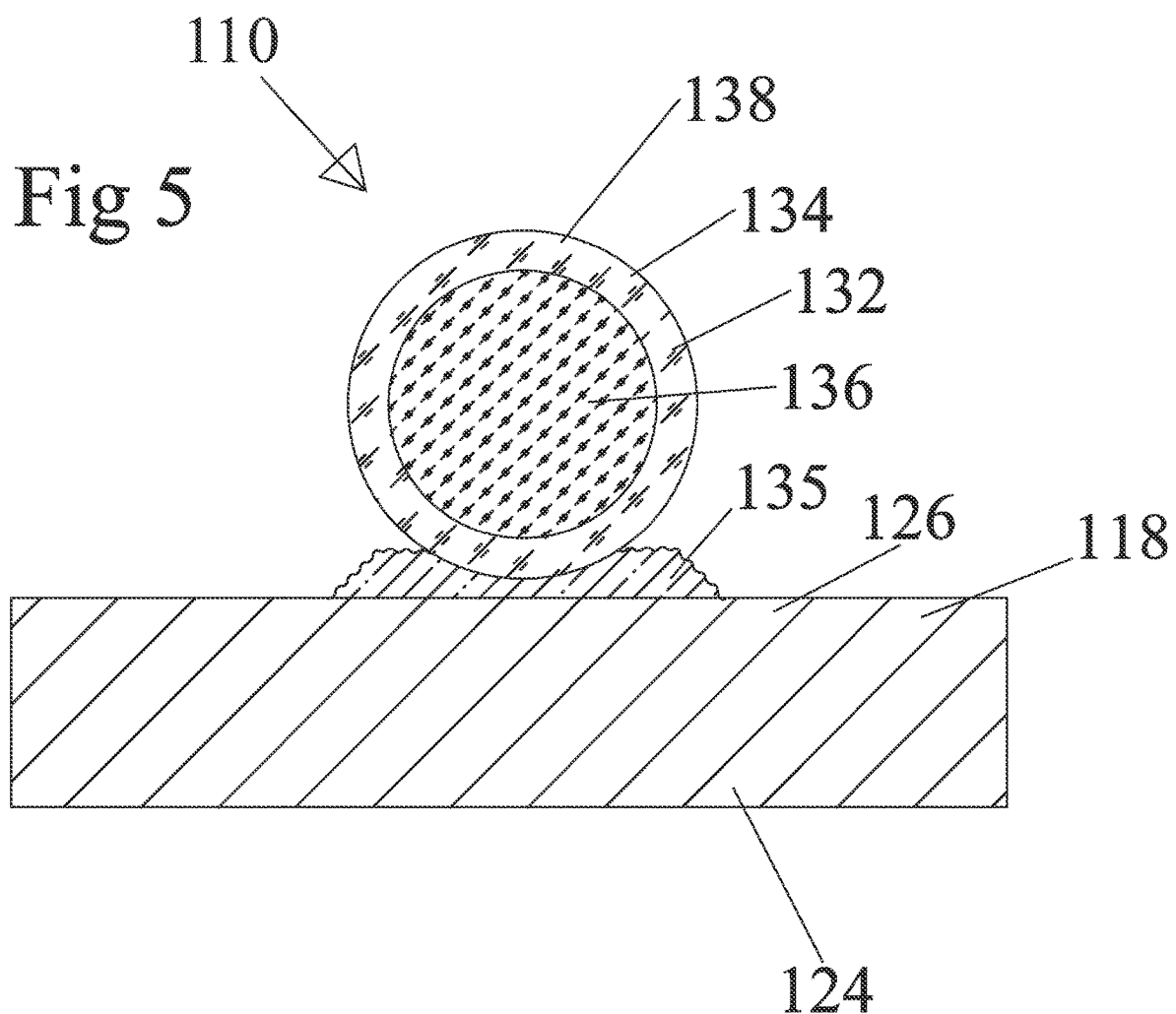
FIG. 5 is a cross-sectional end view of a fiber optic sensor configured in accordance with an embodiment of the present invention.

Referring now to FIGS. 2 and 3, specific aspects of the sensor housing assemblies 106a-106n are presented. As shown in FIG. 2, each of the sensor housing assemblies 106a-106n may include one or more longitudinal strain fiber optic sensors 110, one or more hoop strain fiber optic sensors 112, one or more torsional strain fiber optic sensors 114, and one or more temperature-sensing fiber optic sensors 116. Preferably, a temperature-sensing fiber optic sensor used as a temperature compensation sensor is located in close proximity to associated strain fiber optic sensors, but is isolated from the strain field (e.g., as provided for by the tubular member interface body 118 of the temperature-sensing fiber optic sensor 116 discussed below in reference to FIG. 6).

In preferred embodiments, each one of the fiber optic sensors is integrated into a sensor housing 117 of a respective one of the sensor housing assemblies 106a-106n. Each one of the fiber optic sensors 110-116 has a tubular member interface body 118 that is exposed at an interface surface 119 of the sensor housing 117 that defines a central passage 120 thereof. An exterior surface of the elongated tubular member is engaged with (e.g., bonded to) the tubular member interface body 118. A longitudinal axis of the central passage 120 extends approximately parallel with a longitudinal axis of the elongated tubular member 102. In preferred embodiments, four (4) longitudinal strain fiber optic sensors 110, which are preferably angularly spaced by 90 degrees around the central passage 120 of the sensor housing 117, may be placed within the sensor housing 117 of a respective one of the sensor housing assemblies 106a-106n.

Preferably, the sensor housing 117 is a one-piece structure made from a resilient polymeric material. Examples of such a one-piece structure include, but are not limited to casting structures and molded structures. For allowing the elongated tubular member 102 to be disposed within the central passage 120 of the sensor housing 117, the sensor housing 117 may include a slot 122 or other feature therein for allowing the elongated tubular member 102 to be placed into the' central passage 120 and fixedly secured to the sensor housing 117. To this end, the sensor housing is preferably made in a manner (e.g., made from a resilient material) for enabling a width of the slot 122 or configuration of such other feature to be selectively manipulated (e.g., increased by flexure of the sensor housing 117).

Referring to FIGS. 2-6, the tubular member interface body 118 of each one of the fiber optic sensors (110-116) has a tubular member engagement portion 124 that is exposed at the interface surface 119 of the sensor housing 117 and an optical fiber engagement portion 126 that is within the sensor housing 117. This arrangement allows for the sensor housing 117 and thus the tubular member interface bodies 118 thereof to be engaged with an exterior surface of the elongated tubular member 102. In preferred embodiments, the tubular member interface bodies 118 are bonded to the exterior surface of the elongated tubular member 102 by use of a suitable bonding material. Such a suitable bonding material (e.g., a 2-part epoxy resin or the like) will enable temperature and strain exhibited at the exterior surface of the elongated tubular member 102 to be imparted upon the tubular member interface body(ies) 118 thereof with negligible attenuation. Preferably, the tubular member interface bodies 118 are made from a metallic material that has a coefficient of thermal expansion that is substantially the same as a coefficient of thermal expansion of a material from which the elongated tubular member 102 is made and have a thickness oat optimized required structural integrity with respect to transmission of strain and/or heat transfer.

Figure 6:
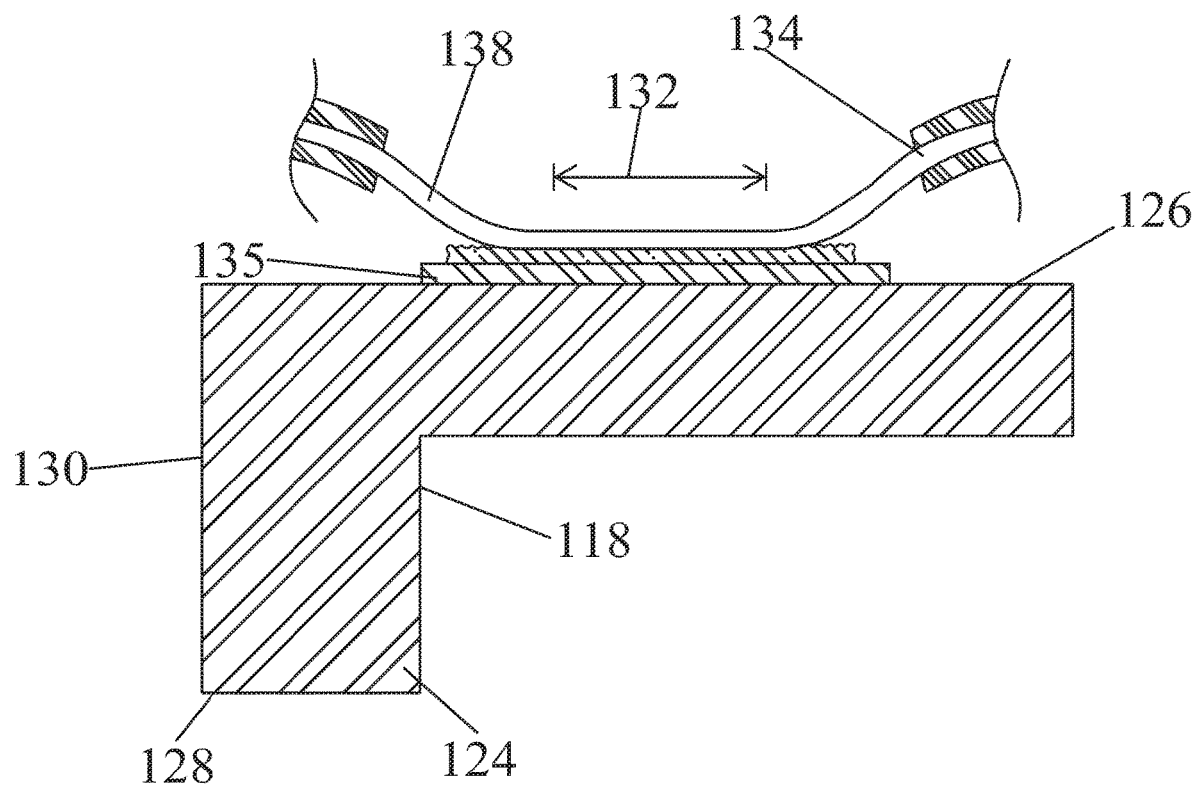
FIG. 6 is a cross-sectional side view of a temperature-indicating fiber optic sensor configured in accordance with an embodiment of the present invention.

As best shown in FIGS. 2-5, each tubular member interface body 118 used for providing strain-specific operating condition information (e.g., of sensors 110-114) preferably has a length that is substantially greater than a width thereof, are orientated with the length direction extending substantially parallel to the direction of the related strain, and have spaced-apart, substantially-parallel opposing major surfaces (i.e., the tubular member engagement portion 124 and the optical fiber engagement portion 126 each define a respective one of the spaced-apart opposing major surfaces). As best shown in FIG. 6, the tubular member interface body 118 used for providing temperature-specific operating condition information (e.g., of sensor 116) is L-shaped and has an end surface 128 and side surface 130 that respectively defining an end face thereof and a side face thereof. The end surface 128 is the tubular member engagement portion 124 and the side surface 130 is the optical fiber engagement portion 126.

As shown in FIGS. 3-6, the optical fiber engagement portion 126 of each tubular member interface body 118 is attached to an optical fiber 134 of the fiberoptic cable 108 at an operating condition signal generating portion 132 thereof. Each tubular member interface body 118 and the attached operating condition signal generating portion 132 of the optical fiber 134 jointly for a respective one of the fiber optic sensor (110-116). Attachment of the optical fiber 134 to the optical fiber engagement portion 126 of the tubular member interface body 118 in combination with the material selection and dimension of the tubular member interface body 118 preferably provides for negligible attenuation of strain events (i.e., expansion-contraction) and thermal events (i.e., temperature change) exhibited at the exterior surface of the elongated tubular member being imparted upon the operating condition signal generating portion 132 of the strain-sensing fiber optic sensors 110-114. To this end, in preferred embodiments, such attachment includes bonding with a suitable bonding material 135 (e.g., a 2-part epoxy resin or the like). Advantageously, fiber optic sensors configured in accordance with embodiments of the present invention involve no penetrations into the elongated tubular member to gain access to operating condition information of a fluid therein. It is disclosed herein that the fiber-optic cable 108 can comprise a plurality of interconnected segments of cable, that the fiberoptic cable 108 can comprise more than one optical fibers, and that the one or more optical fibers of one or more segments of fiber-optic cable can be connected in an end-to-end manner to form a contiguous optical fiber structure.

The optical fiber 134 includes a light transmitting structure 136 (e.g., a cladded core) and a polymeric coating 138 formed directly on the light transmitting structure 136. Polyimide and polyacrylate are examples of such polymeric material. It is disclosed herein that the light transmitting structure 136 (e.g., the core or cladding thereof) can contain Germania and/or Ebrium dopants for signal amplification and can be made of a single mode of silica glass.

Advantageously, the applicants herein have discovered that, when the optical fiber 134 has a polyimide coating, the optical fiber can be bonded directly to the optical fiber engagement portion 126 without removal of such polyimide coating. In contrast, when the optical fiber 134 has a polyacrylate coating, the polyacrylate coating is preferably removed from the light transmitting structure 136 of the optical fiber 134 such that the light transmitting structure 136 of the optical fiber 134 can be bonded directly to the optical fiber engagement portion 126. Without wishing to be bound by any particular theory, applicant believes that one or more mechanical/physical properties of the polyimide material provide for negligible attenuation of strain and thermal events exhibited within the exterior surface of the elongated tubular member 102 being communicated to the operating condition signal generating portion 132 of the optical fiber 134. Examples of such mechanical/physical properties of the polyimide material include, but are not limited to, modulus of elasticity, tensile strength, and coefficient of friction.

The operating condition signal generating portion 132 of the optical fiber 134 is within light transmitting structure 136. In preferred embodiments, the optical fiber 134 includes a plurality of operating condition signal generating portions spaced along its length, whereby each one of the fiber optic sensors 110-116 positioned along a length of the elongated tubular member 102 comprises a respective one of the operating condition signal generating portions. Each operating condition signal generating portion 132 of the optical fiber 134 is configured to interact with a respective different wavelength of light that is transmitted along the length of the optical fiber 134 within the light transmitting structure 136 (i.e., transmitted signal). Such interaction generates a corresponding signal (i.e., detected signal) that characterizes a changes in the strain and/or temperature exhibited within the operating condition signal generating portion 132 with respect to baseline strain and/or temperature. By assessing the detected signal for a particular one of the fiber optic sensors 110-116, operating condition information of the elongated tubular member 102 and/or a fluid therein at a location of the particular one of the fiber optic sensors 110-116 can be determined such as by a suitably configured algorithm of a data acquisition system.

Figure 7:
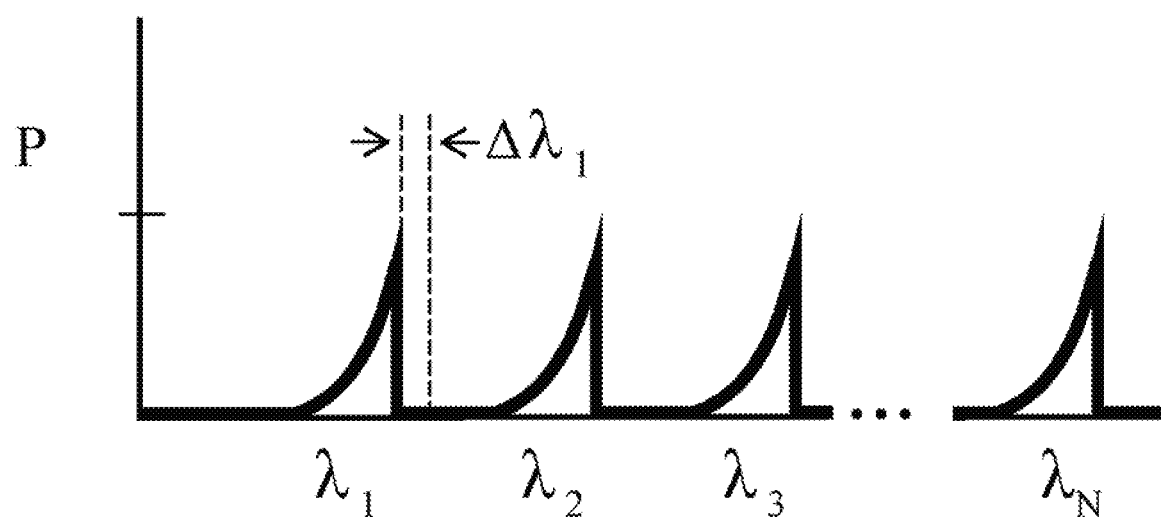
FIG. 7 is a diagrammatic view showing a detected signal in accordance with wavelength division multiplexing for a plurality of fiber optic sensors.

FIG. 7 shows an example of a detected signal in accordance with wavelength division multiplexing for a plurality of fiber optic sensors that each have an operating condition signal generating portion that is responsive to a different wavelength of a transmitted signal (i.e., a pulse of laser light of a known spectrum of wavelength). When the operating condition signal generating portion of each fiber optic sensor is subjected to the transmitted signal, it produces a reflected signal having a power peak 140 at the responsive wavelength thereof for each one of n fiber optic sensors. For example, a data acquisition system configured in accordance with an embodiment of the present invention can claim power greater than 20 dB within an interrogator thereof. The wavelength of the reflected signal for a particular one of the fiber optic sensors shifts higher or lower as a function of changes in length of the operating condition signal generating portion thereof due to expansion and contraction resulting from changes in strain within the elongated tubular member, change in temperature of the elongated tubular member and change in temperature of the operating condition signal generating portion of the optical fiber.

Through use of one or more fiber optic sensors that sense changes in strain within the elongated tubular member and at least one adjacent fiber optic sensor that monitors temperature at the location of the elongated tubular member where the strain-sensing fiber optic sensors are located, one or more of the operating conditions can be derived. Such operating conditions include, but are not limited to, strain within a wall of an elongated tubular members, pressure within an interior space of the elongated tubular members, torsion applied to the elongated tubular members, temperature of the wall or surface of the elongated tubular members, temperature of a fluid within the interior space of the elongated tubular members, and flow confirmation of a fluid within the interior space of the elongated tubular members.

Bragg grating, which are well-known to a person of ordinary skill in the art of optical fibers, is a preferred implementation of the operating condition signal generating portion 132 of the optical fiber 134. Wavelength for the Bragg gratings may range from about 1200 to about 1700 nanometers with reflectively thereon being generally greater than about 10% and preferably greater than about 90%. Although Bragg gratings are a preferred implementation of the operating condition signal generating portion 132, it is disclosed herein that other implementations of generating operating condition information are also contemplated herein. By way of example, such other that other implementations of generating operating condition information include, but are not limited to, distributed strain signal generating techniques, Sagano signal generating techniques, Micheloson signal generating techniques, and Fabry Pero signal generating techniques. It is also disclosed herein that electrical based sensors such as restive strain gauges, accelerometers, and/or potentiometers may optionally be used (e.g., in combination with fiber optic sensors) for generating operating condition information. Furthermore, it is disclosed herein that optical time domain reflectometry methods are integrated into the Bragg gratings or other similarly configured operating condition signal generating portion for temperature monitoring.

Figure 8:
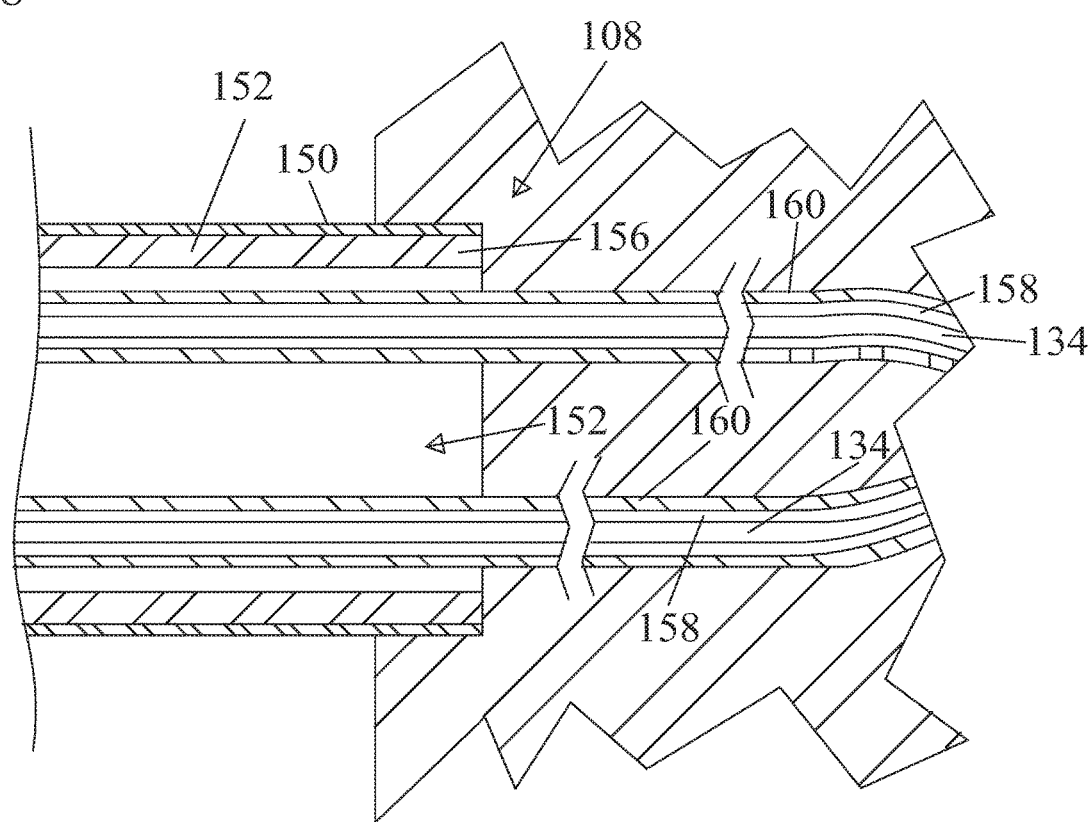
FIG. 8 is a fragmentary cross-sectional view showing a fiberoptic cable configured in accordance with an embodiment of the present invention.

FIG. 8 shows a preferred embodiment of the fiberoptic cable 108. The fiberoptic cable 108 includes an outer jacket 150 formed over a tubular armor layer 152 that is within a central passage 154 of the outer jacket. An end portion 156 of the outer jacket 150 and the tubular armor layer 152 is secured within the sensor housing 117. A plurality of optical fibers 134 extend within the central passage 154. A length of each one of the optical fibers extends beyond the end portion 156 of the outer jacket 150 from within the central passage 154 and into the sensor housing 117. For example, as discussed above in reference to FIGS. 2-6, one or more of the optical fibers 134 has operating condition signal generating portions 132 thereof attached to a respective tubular member interface body 118 for forming the optical fiber sensors 110-116 and, thus, extends beyond the end portion 156 of the outer jacket 150.

Figure 9:
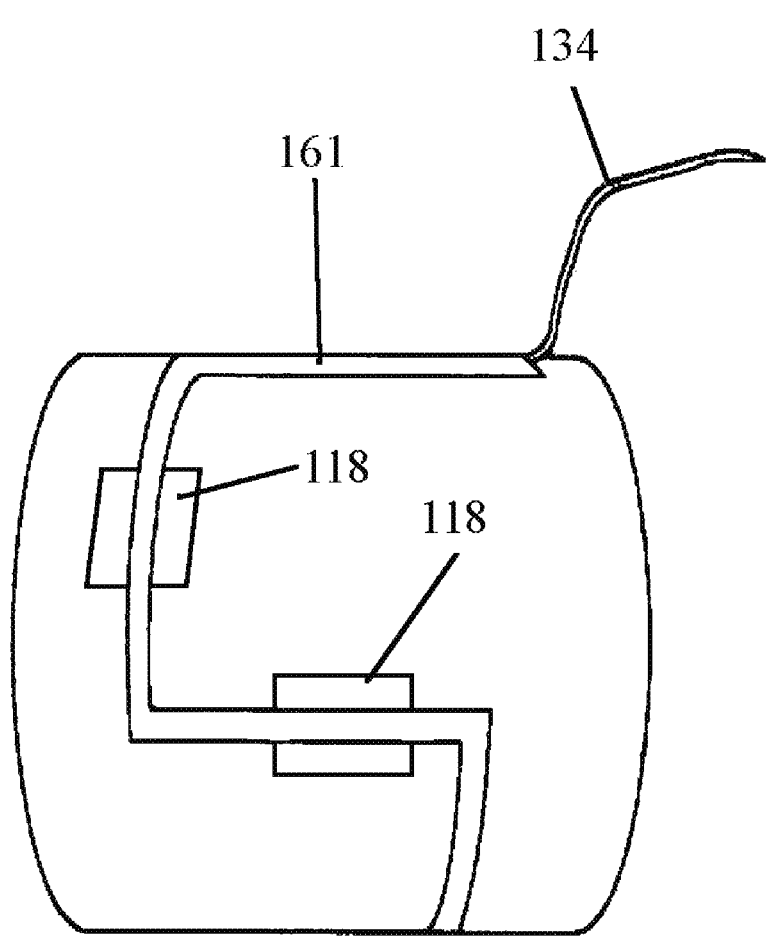
FIG. 9 is a side view showing a length of unjacketed optical fiber extending over an exterior surface of an elongated tubular member and covered by a layer of protective material.

At least a portion of each one of the lengths of the optical fibers that spans between the respective tubular member interface body 118 and the end portion 154 of the outer jacket 150 is disposed within a layer of a viscous material composition 158. The optical fibers 134 can each extend within a respective inner jacket 160. Where the optical fiber 135 extends from the central passage 154 into the sensor housing 117 and is within the inner jacket 160, the viscous material composition 158 is preferably within the inner jacket 160. When the optical fiber 134 extends beyond an end portion of inner jacket 160 and/or there is no inner jacket (i.e., unjacketed optical fiber), a layer of the viscous material composition 158 may be provided onto the optical fiber 134 such as, for example, where it spans over the elongated tubular member 102. For example, as shown in FIG. 9, a length of unjacketed optical fiber 134 extends over the exterior surface of the elongated tubular member 102 and is covered by a layer of protective material 161 (e.g., a layer of polymeric material such as polyurethane). In such case, the length of unjacketed optical fiber 134 is preferably disposed within a layer of the viscous material composition 158.

In applications where the optical fiber is without protection of the tubular armor layer 152 and is subjected to pressure from use in a subsea environment, the applicant has discovered that disposing the optical fiber 132 within a layer of viscous material composition is advantageous. Without wishing to be bound to any specific theory, applicant believes that the layer of viscous material serves as a hydrostatic support that aids in mitigating non-uniform cross-sectional compression of the optical fiber and that aids in limiting the occurrence of 'microbeads' resulting from the optical fiber being forced against small-radius/sharp discontinuities with mating surfaces of the sensor housing 117 or elongated tubular member 102.

The viscous material composition preferably exhibits a relatively uniform level of viscosity across a wide range of temperatures. For example, in a preferred embodiment, the viscous material composition is a grease that has an oil viscosity index of not less than about 120, a temperature range having an upper limit of at least about 200° C., and an oil viscosity of at least about 3.0 at 200° C. Examples of a grease (i.e., a viscous material composition) exhibiting such thermal viscosity stability are commercially-available from E. I. du Pont de Nemours and Company under the tradename and grades of KRYTOX GPL 205(H-1), KRYTOX GPL 206(H-1), KRYTOX GPL 207, KRYTOX GPL 216, KRYTOX GPL 217, KRYTOX GPL 250AC, and KRYTOX GPL280AC.

Applicant has discovered that exposure of optical fibers to pressure of a subsea environment can result in attenuation of a reflected signal within an optical fiber. It is theorized that such attenuation can be due to cross-sectional distortion of the optical fiber such as, for example, resulting from impingement of the optical fiber upon discontinuities that create microbends in the optical fiber, from compression of the optical fiber against otherwise flat, sufficiently rigid surfaces, and the like. The result is a reduction in signal power and distortion of the signal profile, both of which can be detrimental to accurate assessment of operating condition information. As discussed above, the use of a viscous material composition can aid in mitigating such attenuation. Optionally or additionally to use of such viscous material composition, the operating condition signal generating portions of an optical fiber (e.g., a light reflective grating thereof) can be adapted to at least partially mitigate signal attenuation caused by force exerted on the optical fiber by the subsea environment. For example, the operating condition signal generating portions of the optical fiber can be formed such that the light reflecting grating thereof is configured to provide a designated Bragg condition exhibited at an environmental pressure of one atmosphere when the optical fiber is subjected to a pressure exerted thereon by the subsea environment. In preferred embodiments, the environmental pressure corresponds to a subsea depth between about 1000 feet and about 5000 feet. Alternatively, or additionally, the operating condition signal generating portions of the optical fiber can be formed such that the light reflecting grating is adapted to produce a signal having a peak amplitude that is at least about 50 dB and preferably not less than about 10 dB when in an environmental condition of 1 atmosphere.

As discussed above, use of fiber optic sensors in accordance with embodiments of the present invention within a subsea environment can result in attenuation of a reflected signal within an optical fiber used to communication signals to and from such fiber optic sensors. This attenuation is an example of environment-induced signal degradation. To further mitigate such environment-induced signal degradation, apparatuses and systems configured in accordance with embodiments of the present invention can be calibrated to account for the environmental effects (e.g., a subsea environment).

In an embodiment of the present invention, such calibration comprises a plurality of steps. A step is performed for deploying an elongated tubular member in a subsea environment. The elongated tubular member has mounted thereon one or more fiber optic sensors that are each adapted for generating a respective form of operating condition information. In this respect, each one of the fiber optic sensors, which can be configured in the manner discussed above with respect to FIGS. 2-6, is an operating condition sensor. A step is performed for causing an operating condition information signal to be transmitted from the fiber optic sensors to a data acquisition system (which can serve as a calibration apparatus) via one or more optical fibers of a fiberoptic cable. As discussed above, the operating condition information signal can be generated by an operating condition signal generating portion of the one or more optical fibers in response to being exposed to a transmitted signal of a given wavelength bandwidth.

In response to the data acquisition system receiving the operating condition information signal, a step is performed for determining an amount of attenuation of the operating condition information signal with respect to a non-subsea environment. An environment comprising an atmosphere of air at a pressure of 1 atmosphere is an example of the non-subsea environment. In response to determining the amount of attenuation, a step is performed for calibrating signal processing functionality of the data acquisition system as a function of the attenuation of the operating condition information signal with respect to the non-subsea environment. For example, in a preferred embodiment, such calibration offsets at least a portion of the attenuation caused by force exerted on the one or more optical fibers by pressure within the subsea environment. Offsetting at least a portion of the attenuation caused by force exerted on the one or more optical fibers by pressure within the subsea environment can include, for example, offsetting wavelength shift in a signal from the at least one operating condition sensor within the subsea environment as a function of a baseline signal generated by the operating condition sensor at atmospheric (i.e., baseline) conditions. Temperature and pressure are examples of such atmospheric conditions. Such offsetting of the wavelength shift can include, for example, determining wavelength shift in at least one of an axial direction of the elongated tubular member and a hoop direction of the elongated tubular member, offsetting the wavelength shift as a function of a differential between a baseline temperature and a temperature of the subsea environment at a location of the operating condition sensor.

In a preferred embodiment of the present invention, the data acquisition system is adapted to receive a signal comprising operating condition information from a plurality of fiber optic sensors. The data acquisition system, which can comprise an optical sensing module and/or a multiplexing unit with a time division multiplexing module, is adapted to utilize WDM to derive information for a plurality of operating conditions using information received from the plurality of fiber optic sensors. One example of such operating condition information is strain within the exterior wall of the elongated tubular member as a function of a signal wavelength generated by the operating condition signal generating portion of a first one of the fiber optic sensors. Another example of such operating condition information is pressure of a fluid within the central passage of the elongated tubular member as a function of a signal wavelength generated by the operating condition signal generating portion of a second one of the fiber optic sensors. Yet another example of such operating condition information is temperature of the fluid within the central passage of the elongated tubular member as a function of a signal wavelength generated by the operating condition signal generating portion of a third one of the fiber optic sensors.

Figure 10:
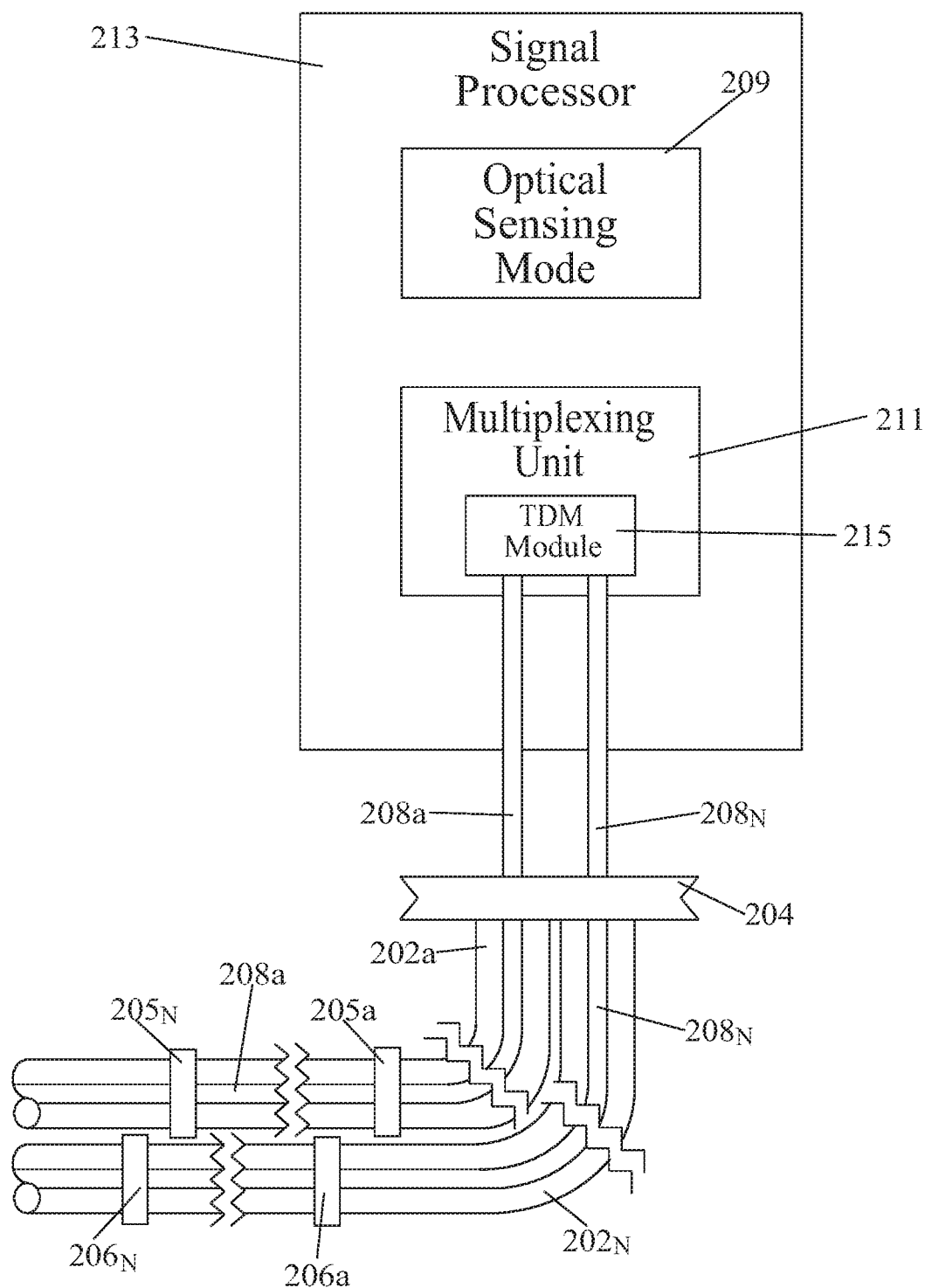
FIG. 10 is a multi-tubular member operating condition monitoring apparatus configured in accordance with an embodiment of the present invention.

Referring now to FIG. 10, a multi-tubular member monitoring apparatus 200 configured in accordance with an embodiment of the present invention is shown. The multi-tubular member monitoring apparatus 200 includes a plurality of elongated tubular member 202 that are connected to a support structure 204. A plurality of sensor housing assemblies 205a-205n, 206a-206n are mounted in a spaced-apart arrangement along a length of a respective one of the elongated tubular members 202a-202n. The sensor housing assemblies 205a-205n, 206a-206n and the fiber optic sensors thereof provide the same or similar functionality as the sensor housing assemblies and the fiber optic sensors discussed above in reference to FIGS. 1-6.

The sensor housing assemblies 205a-205n of a first one of the elongated tubular members 202a by a first optical cable 208a and the sensor housing assemblies 206a-206n of an n-th one of the elongated tubular members 202n are connected to each other by an n-th optical cable 208b. The plurality of fiberoptic cables 1-n are connected to a multiplexing unit (MUX) 211 of a signal processor 213 for enabling signals generated by the sensor housing assemblies 205a-205n, 206a-206n to be provided to the signal processor 213. The MUX 211 is connected to an optical sensing module 209 and includes a Time Division Multiplexing (TDM) module 215. The optical sensing module 209 of FIG. 10, as well as the optical sensing module 107 of FIG. 1, can provide signal processing functionality and calibration functionality, as discussed above.

Figure 11:
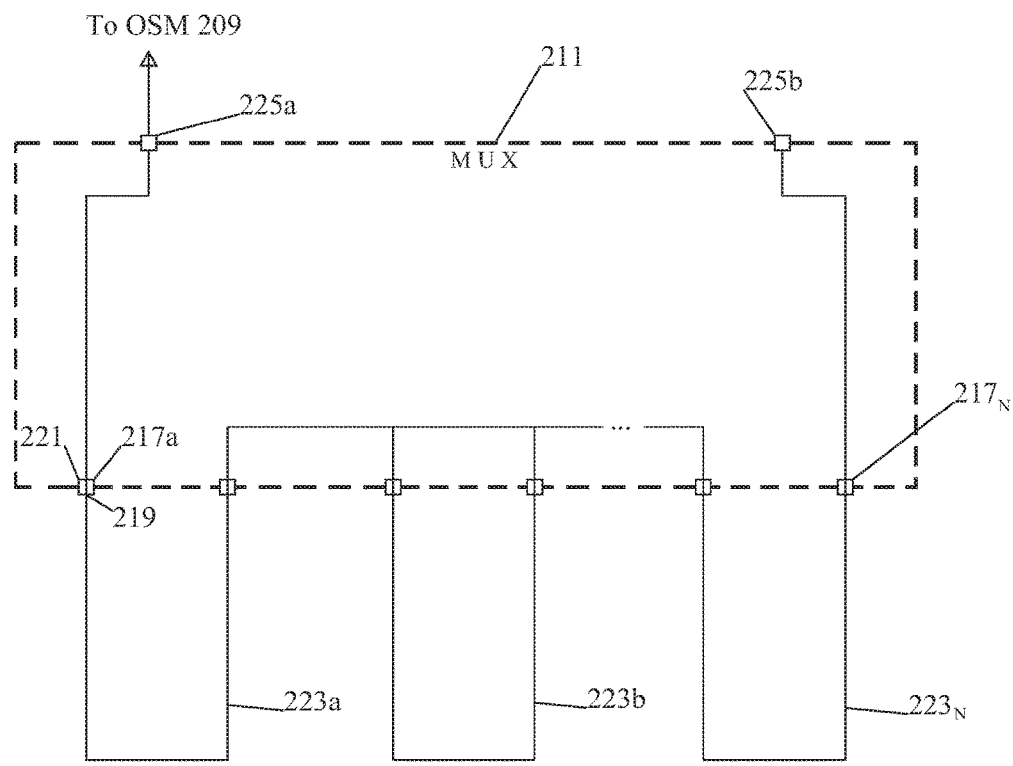
FIG. 11 is a diagrammatic view showing a multiplexing unit providing for signaling via a first end of a contiguous optical fiber structure.

Referring to FIG. 11, the MUX 211 includes a plurality of optical fiber interfaces 217a-217n each having a downstream facing port 219 and an upstream facing port 221. The upstream facing port 219 of each one of the optical fiber interfaces 217a-217n is connectable to each other one of the upstream facing ports 219 for allowing each end of each one of a plurality of optical fibers 223a-223n of one or more fiberoptic cables (e.g., the fiberoptic cables 208a-208n) to be operably connected to the downstream facing port of a respective one of the optical fiber interfaces 217a-217n such that at least two of the optical fibers are connected to each in a series fashion to form a contiguous optical fiber structure having opposing ends. For example, as shown in FIG. 11, the contiguous optical fiber structure comprises the plurality of optical fibers 223a-223n. The upstream facing port connected to an end of the contiguous optical fiber structure is connected to a first signaling port of the optical sensing module 209 via a first signaling port 225a of the MUX 211 for enabling sensor data generated within the contiguous optical fiber structure to be provided from the MUX 211 to the optical sensing module 209.

As shown in FIG. 11, signaling is performed in a conventional manner, which is via a first one of the ends of the contiguous optical fiber structure. Advantageously, however, the MUX 211 and, optionally, the TDM module 215 of the MUX 211 also allow multiple configurations of signal being provided from the first and second fiber optic cables 208, 209 to the optical sensing module 209 in the case where one or more discontinuities occur within the contiguous optical fiber structure.

Figure 12:
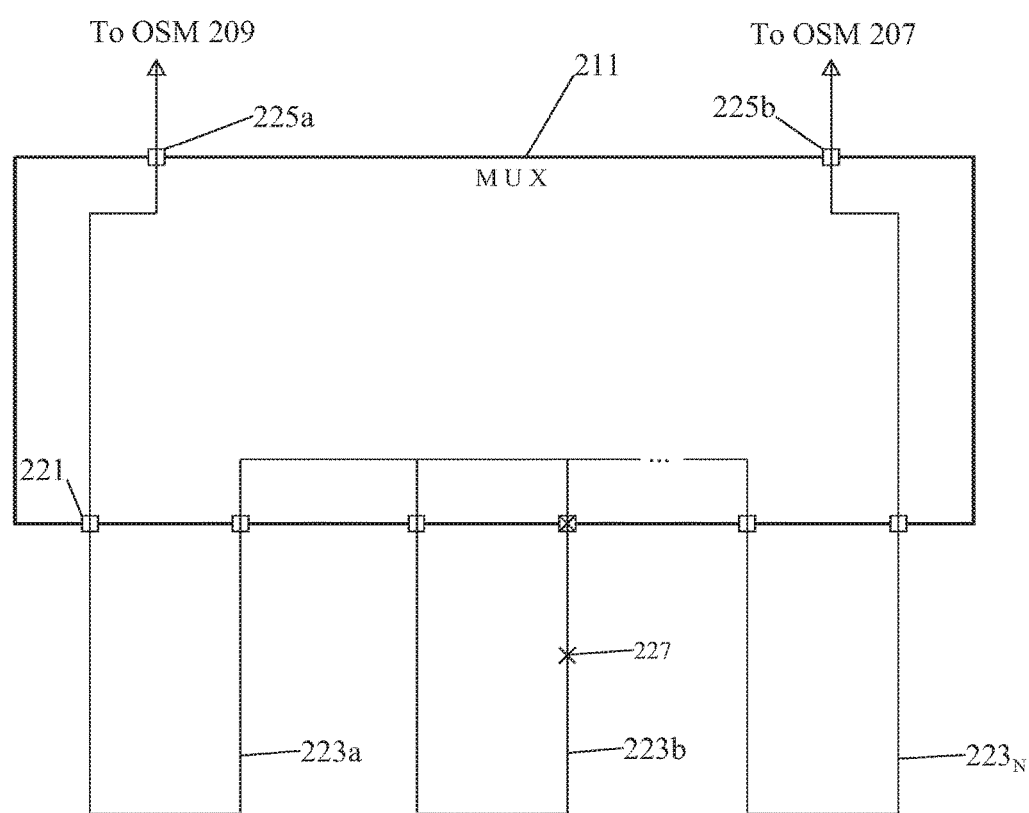
FIG. 12 is a diagrammatic view showing the multiplexing unit of FIG. 11 providing for signaling via both first and second ends of the contiguous optical fiber structure when a discontinuity is detected therein.

As shown in FIG. 12, when a discontinuity 227 occur within a particular one or more of the one optical fibers 223a-223n of the contiguous optical fiber structure (e.g., optical fiber 223b), the MUX 211 may be adapted to implement an operating condition signal to be provided at both of the opposing ends of the contiguous optical fiber structure and monitoring a respective operating condition signal at both of the ends of the contiguous optical fiber structure. For example, in a preferred implementation of the operating condition signal being provided at both of the opposing ends of the contiguous optical fiber structure and monitoring the respective operating condition signal at both of such ends, a first operating condition signal provided via at a first end of the contiguous optical fiber structure and a second operating condition signal provided via at a second end of the contiguous optical fiber structure is monitored by the optical sensing module 209. The TDM module 215 of the MUX 211 can be used for enabling monitoring of the first operating condition signal provided via at the first end of the contiguous optical fiber structure and the second operating condition signal provided via at the second end of the contiguous optical fiber structure via a single signaling port of the optical sensing module 209.

Figure 13:
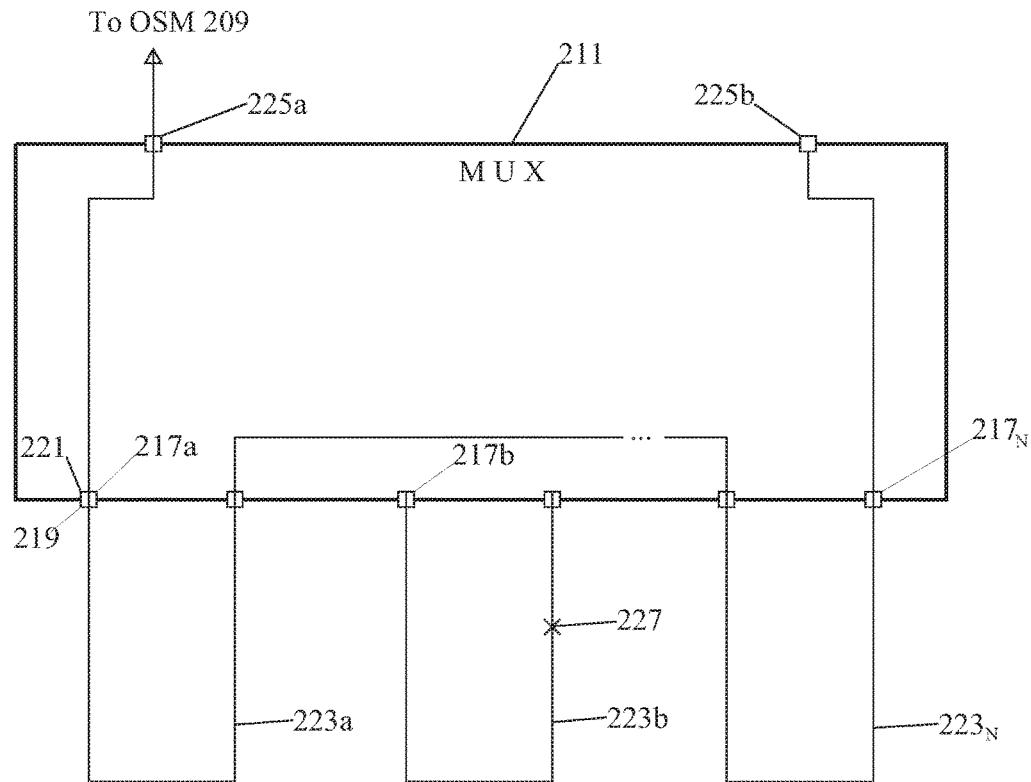
FIG. 13 is a diagrammatic view showing the multiplexing unit of FIG. 11 providing for reconfiguration of constituent lengths of optical fiber of the contiguous optical fiber structure when a discontinuity is detected therein.

Alternatively, as shown in FIG. 13, when the discontinuity 227 occurs within the particular one or more of the optical fibers 223a-223n of the contiguous optical fiber structure (e.g., optical fiber 223b), the MUX 211 may be adapted to implement excluding (e.g., bypass) the particular one or more of the optical fibers 223a-223n from within the contiguous optical fiber structure to create a reconfigured version of the contiguous optical fiber structure and continuing to monitor the operating condition signal provided at the first end of the contiguous optical fiber structure (i.e., via the first signaling port 225a of the MUX). It is disclosed herein that the abovementioned functionalities of the MUX 211 may be implemented manually and/or in an automated manner using optical switches and/or physical couplings. For example, in a preferred implementation of the particular one or more of the optical fibers 223a-223n being excluded from within the contiguous optical fiber structure, detaching the particular one or more of the optical fibers 223a-223n can include detaching first and second ends of the particular one or more of the optical fibers 223a-223n from a corresponding end of adjacent ones of the optical fibers 223a-223n and connecting together the corresponding ends of the adjacent ones of optical fibers 223a-223n.

Figure 14:
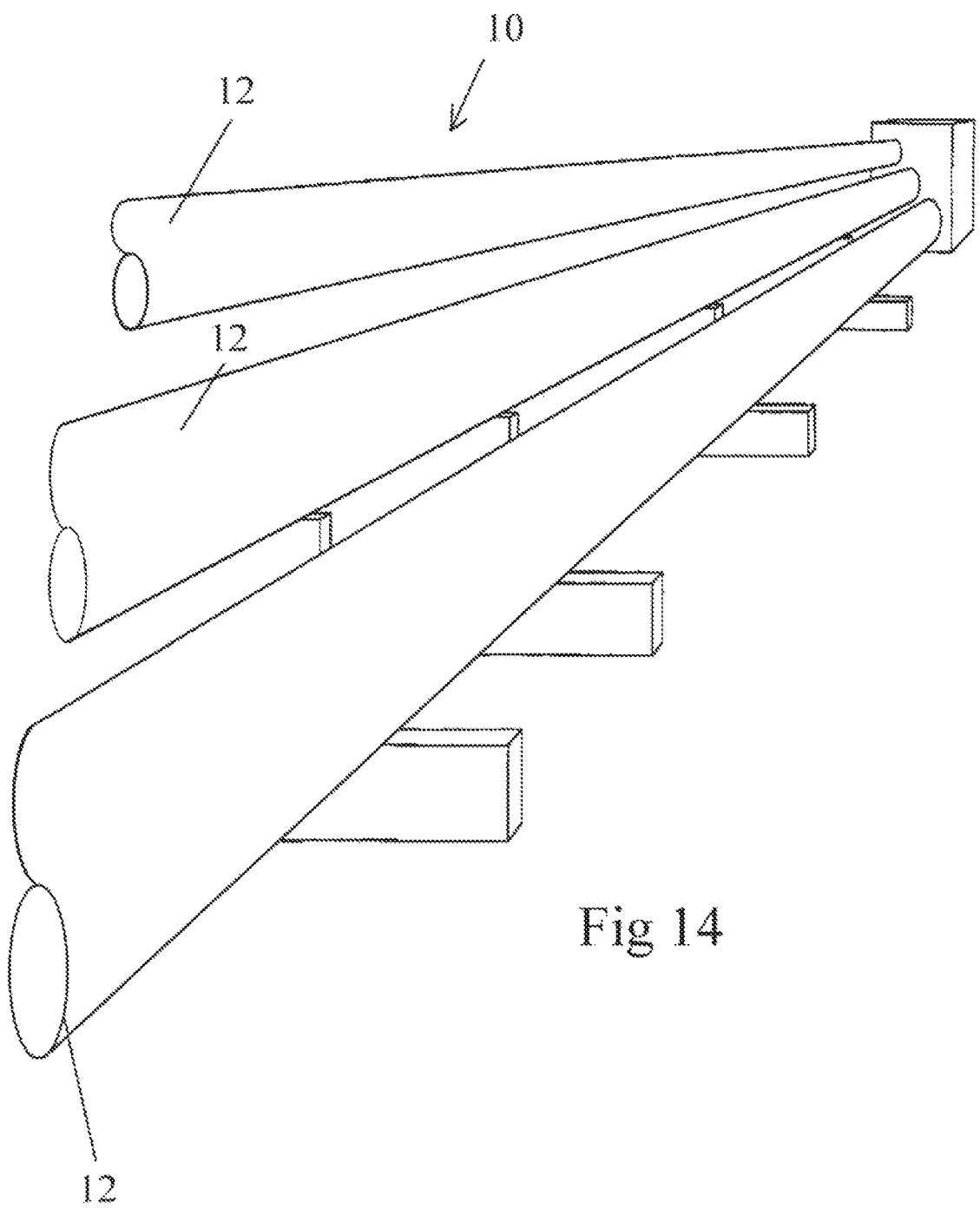
FIG. 14 is a perspective view of a typical pipeline, before deployment in a subsea environment.
Figure 15:
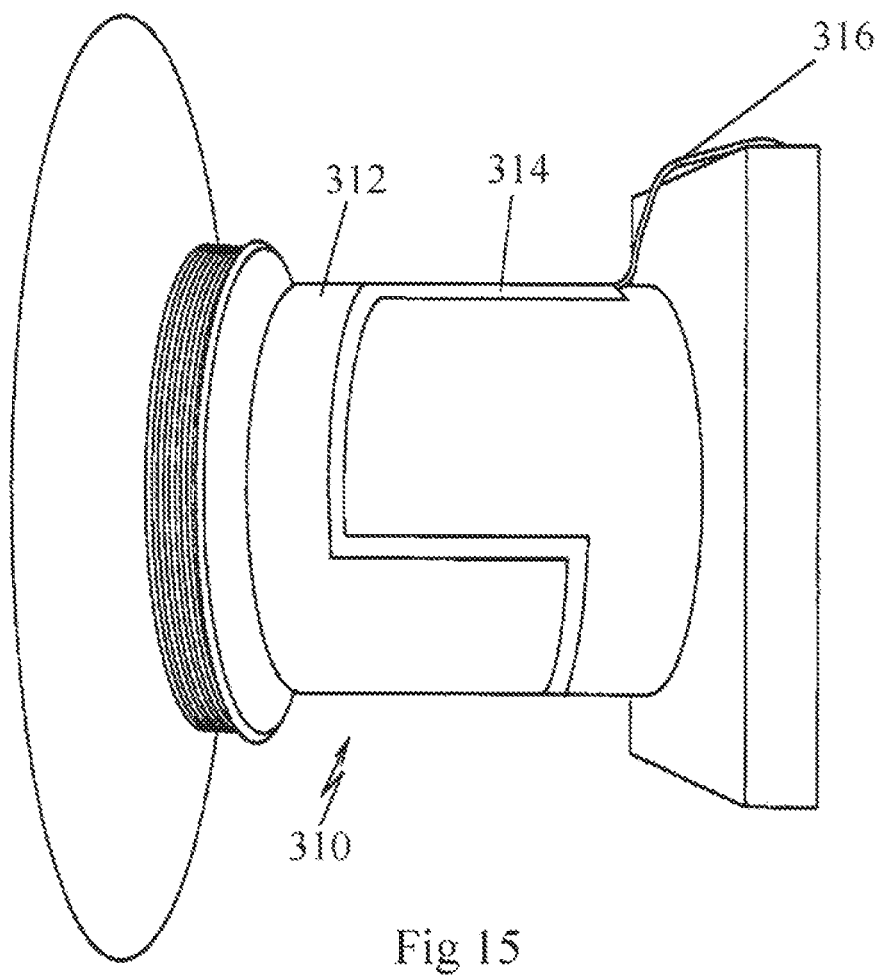
FIG. 15 is a side view showing fiber optic sensors as applied to the exterior wall of the pipeline.
Figure 16:
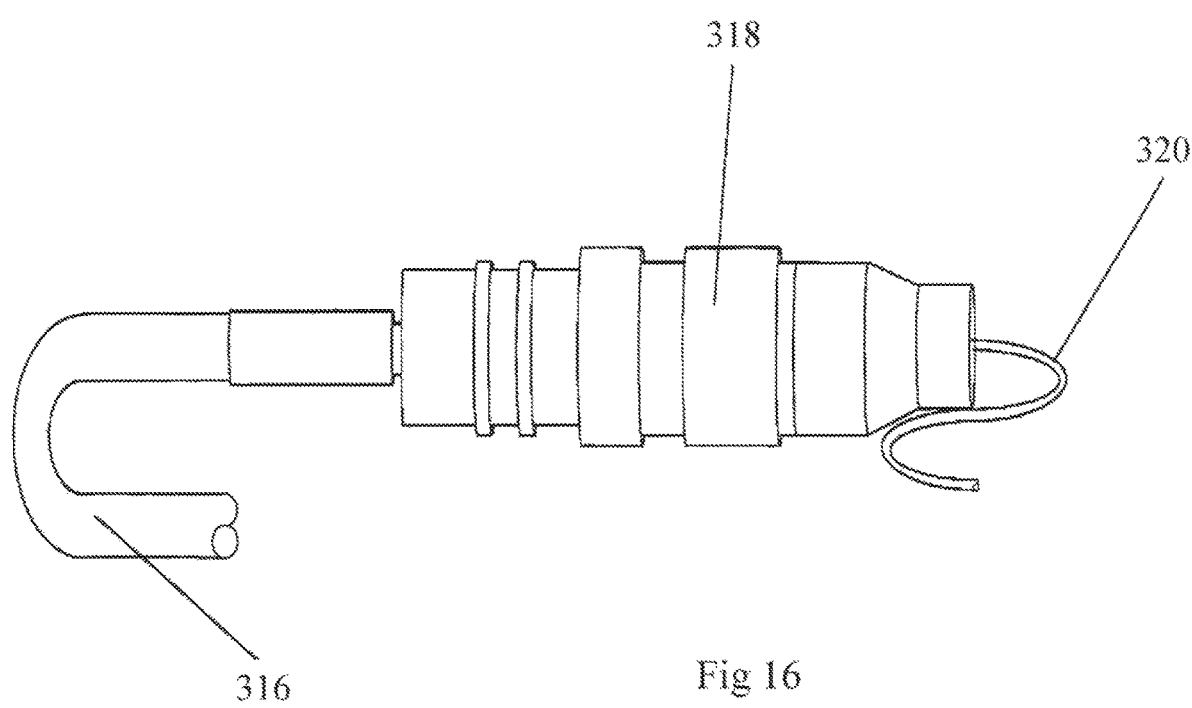
FIG. 16 is a side view showing a collector for collecting the data from a plurality of sensors attached to the pipeline.
Figure 17:
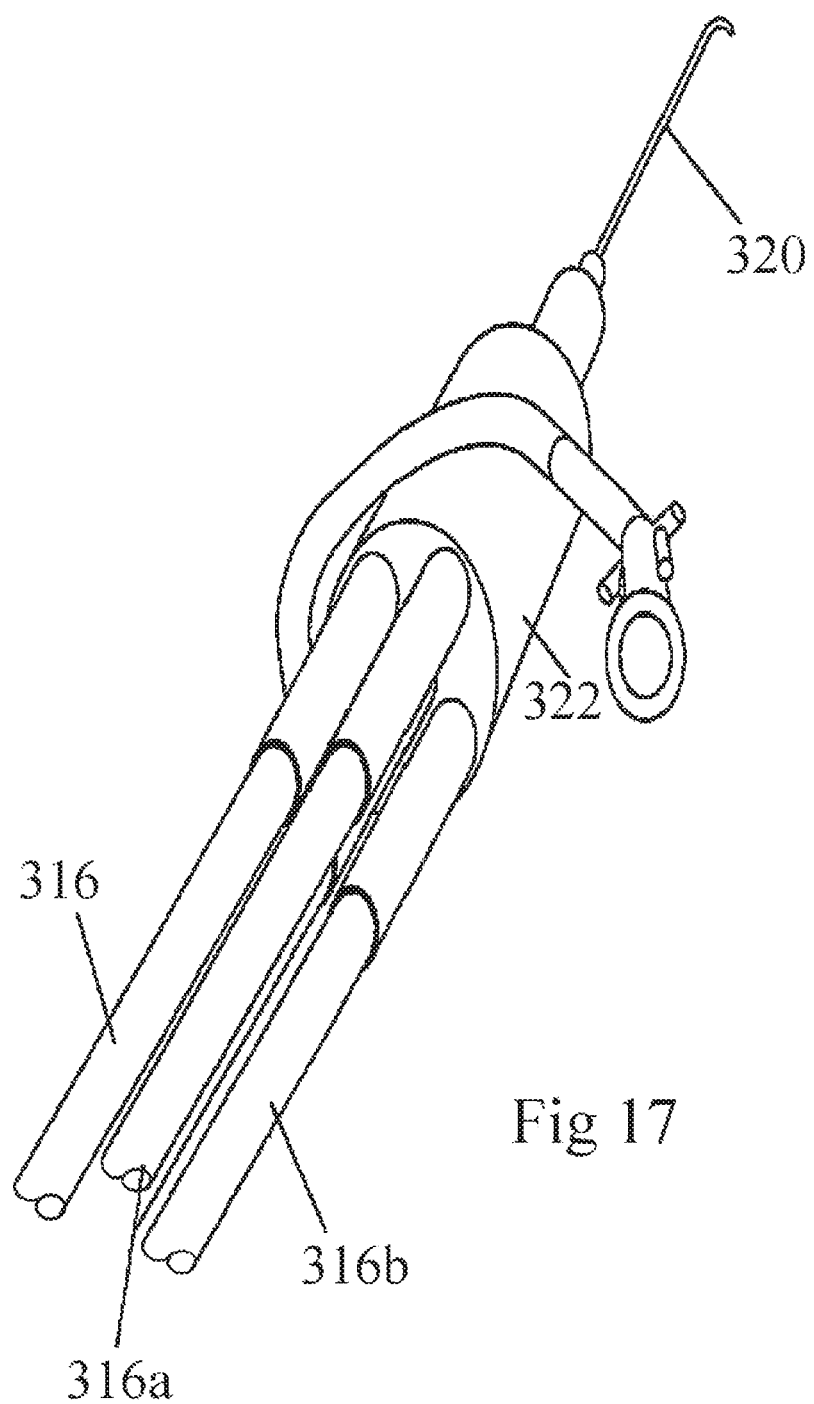
FIG. 17 is a perspective view showing an alternative collector for collecting the data from a plurality of sensors attached to the pipeline.

It is disclosed herein that the above-mentioned MUX functionalities can be implemented in response to a signal assessment process. The signal assessment process may begin with monitoring an operating condition signal provided at one of the ends of the contiguous optical fiber structure to determine operating condition information generated by the operating condition sensors thereof, followed by detecting loss of operating condition information corresponding to at least one of the individual lengths of optical fiber. In response to detecting the loss of operating condition information, the signal assessment process causes reconfiguration of the monitoring of the operating condition signal in accordance with at least one of the above-mentioned MUX functionalities FIGS. 14-17 shown a pipeline system having aspects configured in accordance with one or more embodiments of the present invention. As shown in FIG. 14, a typical pipeline 310 is positioned for deployment in a subsea environment. As discussed above, the fiber optic sensors are attached directly to the outer wall 312 by an epoxy 14, as shown in FIG. 15. The data collected by a sensor array is then conducted to a fiber breakout assembly or collector 318 via the fiber optic cable 316, which is attached to the sensors in the array, as disclosed in FIG. 16. The collected data is then conducted to a topside control room (not shown) via the conductor 320. An alternative collector 322 is shown in FIG. 17, wherein a plurality of sensor array cables 316 may be connected to a single collector 322 for transmitting the collected data to the topside control room via cable 320.

The cabling, connectors, breakout assemblies and support hardware are designed to provide ruggedness during installation and provide attenuation free light transfer. The system is designed for long service life and has measure incorporated to minimize any light transmittal issues such as fiber darkening from hydrogen infusion. Since there are various local measurement locations along the pipeline fiber breakout assemblies incorporated into the invention. Additionally, there is a combination of fiber optic measurements that are integrated into the system.

Preferably, the system contains a multiple of fiber Bragg grating arrays deployed subsea along the pipeline. All tubing is stainless steel. Where desired, Kevlar jackets may be employed.

The time of flight for the light signal is incorporated in the topside monitoring system in the control room.

Attenuation mitigation is used by the use of a pressure balancing material applied to the fiber optic strands in the fiber optic cables. Preferably, the fiber optic cables are coated with a polyurethane, nylon, or polyethylene coating. Polyurethane and epoxy housings are used on top of the sensor stations.

The subsea sensors use hoop displacement of the pipeline the pipeline to determine product pressure from the exterior of the pipeline. No penetrations into the pipeline are necessary to gain access to the flow stream measurements. The connections are designed with a small angled ferrule to minimize back reflections.

Fiber bundles are multi-fused (more than one fusion splice) in each breakout assembly to reduce space requirements.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An apparatus for sensing operating condition information from an elongated tubular member, comprising:
    a plurality of tubular member interface bodies each including a tubular member engagement portion and an optical fiber engagement portion;
    a plurality of optical fibers each having a first end and a second end, wherein two or more of the optical fibers have at least one operating condition signal generating portion between the first and second ends thereof and wherein the at least one operating condition signal generating portion of said two or more of the optical fibers is attached along a length of the optical fiber engagement portion of a respective one of the tubular member interface bodies to thereby form a plurality of operating condition sensors connected to the elongated tubular member;
    an optical sensing module having at least one signaling port; and
    a multiplexing unit including a plurality of optical fiber interfaces each having a downstream facing port and an upstream facing port, wherein the upstream facing port of each one of the optical fiber interfaces is connectable to each other one of the upstream facing ports, wherein each end of each one of the optical fibers is operably connected to the downstream facing port of a respective one of the optical fiber interfaces, wherein the upstream facing ports are connected to each other such that at least two of the optical fibers are connected in a series fashion to form a contiguous optical fiber structure having opposing ends and wherein the upstream facing port connected to an end of the contiguous optical fiber structure is connected to the at least one signaling port of the optical sensing module for enabling sensor data generated within the contiguous optical fiber structure to be provided from the multiplexing unit to the optical sensing module.

2. The apparatus of claim 1 wherein:
    the contiguous optical fiber structure includes a plurality of operating condition signal generating portions that each generate operating condition information when exposed to light provided thereto by the optical sensing module;
    the optical sensing module includes a signal controller, a first signaling port and a second signaling port;
    the signal controller is connected to the first signaling port and to the second signaling port;
    the upstream facing port connected to a first one of the opposing ends of the contiguous optical fiber structure is connected to the first signaling port;
    the upstream facing port connected to a second one of the opposing ends of the contiguous optical fiber structure is connected to the second signaling port; and
    the signal controller is configured to automatically transition from providing signaling functionality at only the first signaling port to provide signaling functionality at both the first and second signaling ports after the optical sensing module determines that an operating condition signal received at the optical sensing module includes operating condition information from less than all of the optical fibers of the contiguous optical fiber structure.

3. The apparatus of claim 2 wherein providing signaling functionality at both the first and second signaling ports includes implementing time division multiplexing at the first and second signaling ports.

4. The apparatus of claim 1 wherein:
    the optical sensing module includes a time division multiplexor;
    the time division multiplexor includes a first signaling port and a second signaling port;
    the upstream facing port connected to a first one of the opposing ends of the contiguous optical fiber structure is connected to the first signaling port;
    the upstream facing port connected to a second one of the opposing ends of the contiguous optical fiber structure is connected to the second signaling port; and
    the time division multiplexor is configured to implement time division multiplexing functionality at the first and second signaling ports after the optical sensing module determines that an operating condition signal received at the first signaling port includes operating condition information from less than all of the optical fibers of the contiguous optical fiber structure.

5. The apparatus of claim 1 wherein:
    the at least one operating condition signal generating portion of each one of two or more optical fibers is located within a subsea environment;
    the optical sensing module and the multiplexing unit are located at a location external to the subsea environment; and
    at least a portion of each one of the optical fibers is configured for limiting signal attenuation resulting from pressure exerted thereon by the subsea environment.

6. The apparatus of claim 5 wherein:
    the at least one operating condition signal generating portion of each one of the optical fibers is located within the subsea environment;

a fiber core of each one of the optical fibers at the operating condition signal generating portion thereof includes a light reflective grating therein; and the light reflecting grating is adapted to at least partially mitigate signal attenuation caused by force exerted on the optical fiber by the environmental pressure within the subsea environment.

7. The apparatus of claim 5 wherein:

each one of the optical fibers includes a light transmitting structure and a layer of polyimide material covering the light transmitting structure;

the layer of polyimide material is applied directly onto the light transmitting structure; and the layer of polyimide material at the operating condition signal generating portion of the optical fiber is bonded directly to the respective one of the tubular member interface bodies.

8. The apparatus of claim 5 wherein:

said optical fibers extend within an internal passage of a fiberoptic cable;

a length of each one of said optical fibers within the subsea environment extends from within the outer jacket of the fiberoptic cable; and at least a portion of each one of the lengths of said optical fibers that extends from within the outer jacket is disposed within a layer of a viscous material composition.

9. The apparatus of claim 1 wherein at least one of the optical sensing module and the multiplexing unit is adapted for:

monitoring an operating condition signal provided at one of opposing ends of the contiguous optical fiber structure to determine operating condition information generated by the plurality of operating condition sensors;

detecting, via the operating condition signal, loss of operating condition information corresponding to at least one of the optical fibers; and in response to detecting the loss of operating condition information, reconfiguring monitoring of the operating condition signal, wherein reconfiguring said monitoring includes one of:

causing an operating condition signal to be provided at both of said opposing ends of the contiguous optical fiber structure and monitoring a respective operating condition signal at both of said ends of the contiguous optical fiber structure; and excluding the at least one of the optical fibers from within the contiguous optical fiber structure to create a reconfigured version of the contiguous optical fiber structure and continuing to monitor the operating condition signal provided at said one of the opposing ends of the contiguous optical fiber structure.

10. The apparatus of claim 9 wherein causing the operating condition signal to be provided at both of said opposing ends of the contiguous optical fiber structure and monitoring the respective operating condition signal at both of said ends of the contiguous optical fiber structure includes:

monitoring a first operating condition signal provided via at a first end of the contiguous optical fiber structure that is connected to a first signaling port of the optical sensing module; and monitoring a second operating condition signal provided via at a second end of the contiguous optical fiber structure that is connected to a second signaling port of the optical sensing module.

11. The apparatus of claim 10 wherein monitoring the first and second operating condition signals is performed using time division multiplexing at the first and second signaling ports.

12. The apparatus of claim 9 wherein excluding the at least one of the individual lengths of optical fiber from within the contiguous optical fiber structure includes:

detaching first and second ends of the at least one of the optical fibers from a corresponding end of adjacent ones of the optical fibers; and connecting together the corresponding ends of the adjacent ones of the optical fibers.

13. The apparatus of claim 12 wherein detaching the first and second ends of the at least one of the optical fibers and connecting together the corresponding ends of the adjacent ones of the optical fibers is performed within a multiplexing unit within which at least one of the ends of a particular one of the optical fibers is attached to an end of another one of the optical fibers to form the contiguous optical fiber structure.

* * * * *